(12) United States Patent
Daute et al.

(10) Patent No.: US 6,649,585 B1
(45) Date of Patent: Nov. 18, 2003

(54) PROCESSES FOR PREPARING SUPERBASIC ZINC SOAPS AND METHODS OF USING SAID SOAPS

(75) Inventors: Peter Daute, Beverstedt (DE); Joerg-Dieter Klamann, Bremerhaven (DE); Peter Wedl, Bremerhaven (DE); Ralf Picard, Bremerhaven (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 0 days.

(21) Appl. No.: 09/890,540

(22) PCT Filed: Jan. 22, 2000

(86) PCT No.: PCT/EP00/00466
§ 371 (c)(1),
(2), (4) Date: Dec. 10, 2001

(87) PCT Pub. No.: WO00/46173
PCT Pub. Date: Aug. 10, 2000

(30) Foreign Application Priority Data

Feb. 3, 1999 (DE) .......................................... 199 04 139

(51) Int. Cl.$^7$ ........................... C11D 13/00; C11D 15/00
(52) U.S. Cl. .................. 510/458; 510/459; 510/481; 510/488; 510/508; 508/460; 106/1.17
(58) Field of Search ................. 510/141, 152, 510/153, 155, 458, 488, 459, 481; 260/413, 414; 508/460; 106/1.17

(56) References Cited

U.S. PATENT DOCUMENTS 4,307,027 A * 12/1981 Borzelli et al. ............. 260/413
4,824,585 A    4/1989 Marotel et al.

FOREIGN PATENT DOCUMENTS

| EP | 0 234 149 A1 | 9/1987 |
| GB | 1142195 A | 2/1969 |
| GB | 2 110 697 A | 6/1983 |
| WO | WO95/34524 | 12/1995 |

OTHER PUBLICATIONS

Ullmann's Encyklopädie der Technischen Chemie, 4th Edition, vol. 21, Verlag Chemie, Weinheim, (1982), p. 224 *NMO.

* cited by examiner

*Primary Examiner*—Necholus Ogden
(74) *Attorney, Agent, or Firm*—John E. Drach; Aaron R. Ettelman

(57) ABSTRACT

Processes for preparing superbasic zinc soaps are disclosed. The processes described comprise: (a) providing a basic zinc carbonate; (b) providing at least one organic carboxylic acid; and (c) reacting the basic zinc carbonate and the at least one organic carboxylic acid at a temperature of from about 100° C. to about 200° C. The use of such soaps for stabilizing halogen-containing plastic compositions is also described.

22 Claims, No Drawings

PROCESSES FOR PREPARING SUPERBASIC ZINC SOAPS AND METHODS OF USING SAID SOAPS

BACKGROUND OF THE INVENTION

Metal soaps are normally produced by directly reacting metal oxides or metal hydroxides with the corresponding organic carboxylic acids or by double decomposition where metal soaps are precipitated from hot aqueous or aqueous/alcoholic soap solution by addition of salt solutions of the particular metals (see, for example, Ullmann's Encyklopädie der Technischen Chemie, 4th Edition, Vol. 21, page 224).

EP-B-0 234 149 describes a process for the production of superbasic calcium soaps in which an oxide and/or a hydroxide of calcium is/are reacted with carbon dioxide, which is injected into the reaction medium, and at least one organic carboxylic acid in the presence of at least one promoter and at least one catalyst and the water formed is removed, the reaction being carried out in an least one organic solvent at temperatures of 80 to 120° C., the organic carboxylic acid containing 7 to 13 carbon atoms and having a linear acid content of 40% by weight or less, a content of acids branched at C-2 of 20% by weight or less and a content of acids branched at C-3 and/or C-n of 40% by weight or more and the organic solvent being replaced by an oil or a mixture of oils at the end of the reaction. The promoter is intended to bind the carbon dioxide.

WO 95/34524 describes a process for the production of superbasic zinc soaps in which a zinc oxide and/or hydroxide is reacted while stirring with gaseous carbon dioxide and at least one organic carboxylic acid. The reaction takes place in the presence of at least one promoter which is intended make carbon dioxide easier to bind. In addition, the water formed during the reaction is said to be continuously removed. The reaction is preferably carried out at temperatures of 80 to 120° C. and in the presence of at least one organic solvent.

BRIEF SUMMARY OF THE INVENTION

The present invention relates, in general, to processes for the production of superbasic zinc soaps in which basic zinc carbonate and an organic carboxylic acid are directly reacted with one another. The processes may be conducted in the absence of organic solvents. The superbasic zinc soaps produced in accordance with the process of the present invention are useful as additives in plastics processing.

It has now been found that superbasic zinc soaps can readily be obtained by directly reacting zinc hydroxycarbonate (basic zinc carbonate) with organic carboxylic acids. The reaction is carried out at temperatures in the range from 100 to 200° C.

The present invention relates to a process for the production of superbasic zinc soaps, characterized in that zinc hydroxycarbonate is reacted with organic carboxylic acids containing 6 to 22 carbon atoms at temperatures of 100 to 200° C. in the absence of organic solvents and the water of reaction formed is continuously distilled off.

The process according to the invention can be carried out much more easily than the processes known from the prior art. In particular, there is no need to use gaseous carbon dioxide in the production of the superbasic zinc soaps. There is also no need to use special promoters to facilitate the binding of carbon dioxide. In addition, according to the invention, the reaction is carried out in a melt of zinc hydroxycarbonate and organic carboxylic acids. Accordingly, there is no need either for a solvent to be used and subsequently removed.

DETAILED DESCRIPTION OF THE INVENTION

Basic zinc carbonate is formed when neutral zinc carbonate, $ZnCO_3$, is reacted with water. Basic zinc carbonate occurs naturally as hydrozincite with the composition $Zn_5[(OH)_3(CO_3)]_2$, but is also commercially available.

As already mentioned, the process according to the invention is carried out at temperatures in the range from 100 to 200° C. In a preferred embodiment, it is carried out at temperatures of 110 to 160° C. and more particularly at temperatures of 130 to 150° C.

As already mentioned, organic carboxylic acids containing 6 to 22 carbon atoms are used in the process according to the invention. These acids may be saturated or unsaturated, linear or branched. They may be used either individually or as a mixture of two or more fatty acids. Examples of suitable organic carboxylic acids containing 6 to 22 carbon atoms are caproic acid, oenanthic acid, caprylic acid, pelargonic acid, capric acid, undecanoic acid, lauric acid, tridecanoic acid, myristic acid, pentadecanoic acid, palmitic acid, heptadecanoic acid, stearic acid, nonadecanoic acid, arachic acid, heneicosanoic acid, behenic acid, 10-undecenoic acid, lauroleic acid, myristoleic acid, palmitoleic acid, oleic acid, petroselic acid, elaidic acid, ricinoleic acid, 12-hydroxystearic acid, 9,10-dihydroxystearic acid, 9,10,11,12-tetrahydroxystearic acid, linoleic acid, linolaidic acid, linolenic acid, elaeostearic acid, gadoleic acid, arachidonic acid, erucic acid, brassidic acid, clupanodonic acid.

One embodiment is characterized by the use of one or more organic carboxylic acids containing 6 to 22 carbon atoms, the content of linear carboxylic acids being at least 90% by weight, based on the total quantity of carboxylic acids used. At least 60% by weight of these linear carboxylic acids are saturated.

Another embodiment is characterized by the use of one or more organic carboxylic acids containing 6 to 22 carbon atoms, the content of acids branched at C-2 being at least 90% by weight, based on the total quantity of carboxylic acids used. 2-Ethylhexanoic acid is preferably used.

Basically, the are no limitations to the ratio in which the two reaction components, i.e. on the one hand the zinc hydroxycarbonate and on the other hand the organic carboxylic acids, are reacted with one another in the process according to the invention. However, the two components are preferably used in such a quantity that the equivalent ratio of OH to COOH is in the range from 0.5:1 to 10:1 and more particularly in the range from 0.5:1 to 2:1. In one particularly preferred embodiment, an equivalent ratio of about 1:1 is adjusted.

The expression "equivalent ratio" is familiar to the expert. The basic concept behind the notion of equivalence is that, for every substance involved in a reaction, the reactive groups participating in that reaction are considered. The indication of an equivalent ratio expresses the numerical ratio which all the reactive groups of the compounds used bear to one another. In the present case, this means the following: basic zinc carbonate is represented by the formula $[ZnCO_3]_2x[Zn(OH)_2]_3$. The organic carboxylic acids are represented by the formula $C_{5-21}$—COOH where $C_{5-21}$ is an alkyl group containing 5 to 21 carbon atoms. An equivalent OH:COOH ratio of 1:1 thus means that the basic zinc carbonate is reacted with the organic carboxylic acid in such a quantity ratio that there are as many OH groups in the zinc hydroxycarbonate used as there are COOH groups in the organic carboxylic acid used. Since, according to the above formula, basic zinc carbonate contains six OH groups, whereas the organic carboxylic acid contains only one COOH group, basic zinc carbonate and organic carboxylic acid must be used in a molar ratio of 1:6.

The present invention also relates to superbasic zinc soaps obtainable by reacting basic zinc carbonate with organic carboxylic acids containing 6 to 22 carbon atoms at temperatures in the range from 100 to 200° C. in the absence of organic solvents and distilling off the water of reaction formed, the content of linear acids being at least 90% by weight, based on the total quantity of carboxylic acids used, and at least 60% by weight of these linear acids being saturated.

The present invention also relates to the use of the superbasic zinc soaps obtainable by the process according to the invention as additives for the processing of plastics and, more particularly, for stabilizing halogen-containing plastics against thermal and/or photochemical degradation.

The superbasic zinc soaps obtainable by the process according to the invention are suitable as additives for stabilizing halogen-containing organic plastics, more especially polyvinyl chloride (PVC).

EXAMPLES

A. Production of Superbasic Zinc Soaps

Example 1
Production of Zinc Carbonate Stearate 162 g (0.6 mol) of technical stearic acid with an acid value of 208 were heated with stirring to 140° C. 54.9 g (0.1 mol) of basic zinc carbonate with the formula $[ZnCO_3]_2 \cdot x[Zn(OH)_2]_3$ (supplier: Fluka) were then added over a period of 10 minutes. The water of reaction formed escaped with foaming over a period of 30 minutes. The slightly whitish melt was heated for another 1.5 hours to 130 to 140° C. and then cooled to 200C.

A white wax-like material was obtained. The analytical data of this material were as follows: zinc content 16.4% by weight; melting point 118°C.; acid value 9.8.

Example 2
Production of Zinc Carbonate Ethyl Hexanoate

The procedure was as in Example 1 except that the stearic acid was replaced by 2-ethylhexanoic acid (0. 6 mol). The paste-like material had a zinc content of 23.7% by weight.

Example 3
Production of Zinc Carbonate Octoate

The procedure was as in Example 1 except that the stearic acid was replaced by n-octanoic acid (0.6 mol). The melting point of the material obtained was determined as 97° C. It had a zinc content of 25.3% by weight.

Example 4
Production of Zinc Carbonate Laurate

The procedure was as in Example 1 except that the stearic acid was replaced by lauric acid (0.6 mol). The melting point of the material obtained was determined as 113° C. It had a zinc content of 20.8% by weight.

B. Performance Tests

The substances obtained in accordance with Examples 1 to 4 were tested for their ability to improve the color stability of polyvinyl chloride (PVC). To this end, the method for measuring color explained below was carried out, special test specimens being heated at 190° C. and the time pattern of the color values being recorded.

Sheeted-out compounds from which test strips were cut out were used as the test specimens. The production of the sheeted-out compounds was based on the following test formulation:

| | |
|---|---|
| PVC (Solvic 271 GC; supplier; Solvay) | 100.0 parts by weight |
| Dioctyl phthalate | 40.0 parts by weight |
| Edenol D 81 (epoxidized soybean oil; supplier: Henkel KGaA) | 4.0 parts by weight |
| Chalk | 30.0 parts by weight |
| Titanium dioxide | 3.0 parts by weight |
| Zinc-free stabilizer | 1.96 parts by weight |
| Test substance[a] | x parts by weight |

[a]Test substance = substances produced in accordance with Examples 1 to 4

The test specimens were produced by homogenizing and plasticizing the rigid PVC and the additives mentioned on a laboratory roller mill for 5 minutes at 170° C. 15 mm wide test strips were then cut out from the ca. 0.5 mm thick sheets thus produced.

The color of the sheeted-out compounds was determined immediately after their production (so-called initial color, t=0). The $L^*,a^*,b^*$-method known to the expert (cf. DIN 6174) was used for this purpose. The $b^*$ value indicates the position on the blue/yellow axis. Normally, the $b^*$ value is also known as the yellow value. A commercially available instrument ("Micro-Color", manufacturer: Dr. Lange) was used for the measurements. The initial colors are set out in Table 1. Table 1 also contains data as to the quantity of test substance present in the test formulation mentioned above. The test strips were then heated at 190° C. in a thermo-oven and were briefly withdrawn from the oven at 15-minute intervals to determine the particular $b^*$ value. The corresponding $b^*$ values measured after 15, 30,45 and 60 minutes are also set out in Table 1.

TABLE 1

| Test substance | $X^b$ | $b^*/0^c$ | $b^*/15^d$ | $b^*/30^e$ | $b^*/45^f$ | $b^*/60^g$ |
|---|---|---|---|---|---|---|
| Example 1 | 0.84 | 6.4 | 9.4 | 11.4 | 13.4 | 17.7 |
| Example 2 | 0.58 | 6.2 | 9.5 | 11.1 | 14.6 | 19.5 |
| Example 3 | 0.55 | 6.3 | 9.4 | 11.7 | 13.9 | 20.4 |
| Example 4 | 0.60 | 6.3 | 9.4 | 11.4 | 14.2 | 20.9 |

[b]X = quantity of test substance in parts by weight in the above-mentioned test formulation (the compounds of Examples 1 to 4 were used with the same percentage of Zn)
[c]$b^*/0$ = initial color (yellow value $b^*$ after 0 minute heating)
[d]$b^*/15$ = yellow value $b^*$ after 15 minutes' heating at 190° C.
[e]$b^*/30$ = yellow value $b^*$ after 30 minutes' heating at 190° C.
[f]$b^*/45$ = yellow value $b^*$ after 45 minutes' heating at 190° C.
[g]$b^*/60$ = yellow value $b^*$ after 60 minutes' heating at 190° C.

What is claimed is:

1. A process for preparing a superbasic zinc soap, said process comprising:
    (a) providing a basic zinc carbonate;
    (b) providing at least one organic carboxylic acid; and
    (c) reacting the basic zinc carbonate and the at least one organic carboxylic acid at a temperature of from about 100° C. to about 200° C., to form a superbasic zinc soap.

2. The process according to claim 1, wherein the basic zinc carbonate and the at least one organic carboxylic acid are reacted at a temperature of from about 110°C. to about 160° C.

3. The process according to claim 1, wherein the basic zinc carbonate and the at least one organic carboxylic acid are reacted at a temperature of from about 130° C. to about 150° C.

4. The process according to claim 1, wherein the at least one carboxylic acid comprises a mixture of two or more organic carboxylic acids.

5. The process according to claim 4, wherein the mixture comprises a linear carboxylic acid component in an amount of at least 90% by weight, based on the weight of the mixture.

6. The process according to claim 5, wherein at least 60% by weight of the linear carboxylic acid component is saturated.

7. The process according to claim 5, wherein the linear carboxylic acid component comprises an acid selected from the group consisting of lauric acid, palmitic acid, stearic acid and mixtures thereof.

8. The process according to claim 4, wherein the mixture comprises a branched carboxylic acid component, branched at C-2, in an amount of at least 90% by weight, based on the weight of the mixture.

9. The process according to claim 8, wherein the branched carboxylic acid component comprises 2-ethythexanoic acid.

10. The process according to claim 2, wherein the at least one carboxylic acid comprises a mixture of two or more organic carboxylic acids.

11. The process according to claim 10, wherein the mixture comprises a linear carboxylic acid component in an amount of at least 90% by weight, based on the weight of the mixture.

12. The process according to claim 11, wherein at least 60% by weight of the linear carboxylic acid component is saturated.

13. The process according to claim 11, wherein the linear carboxylic acid component comprises an acid selected from the group consisting of lauric acid, palmitic acid, stearic acid and mixtures thereof.

14. The process according to claim 10, wherein the mixture comprises a branched carboxylic acid component, branched at C-2, in an amount of at least 90% by weight, based on the weight of the mixture.

15. The process according to claim 14, wherein the branched carboxylic acid component comprises 2-ethylhexanoic acid.

16. The process according to claim 1, wherein the basic zinc carbonate and the at least one organic carboxylic acid are reacted at an OH:COOH equivalent ratio of from 0.5:1 to 10:1.

17. The process according to claim 1, wherein the basic zinc carbonate and the at least one organic carboxylic acid are reacted at an OH:COOH equivalent ratio of from 0.5:1 to 2:1.

18. The process according to claim 2, wherein the basic zinc carbonate and the at least one organic carboxylic acid are reacted at an OH:COOH equivalent ratio of from 0.5:1 to 2:1.

19. The process according to claim 4, wherein the basic zinc carbonate and the at least one organic carboxylic acid are reacted at an OH:COOH equivalent ratio of from 0.5:1 to 2:1.

20. The process according to claim 10, wherein the basic zinc carbonate and the at least one organic carboxylic acid are reacted at an OH:COOH equivalent ratio of from 0.5:1 to 2:1.

21. A process for preparing a superbasic zinc soap, said process comprising:

(a) providing a basic zinc carbonate;

(b) providing a mixture of two or more organic carboxylic acids, wherein the mixture comprises a linear carboxylic acid component in an amount of at least 90% by weight, based on the weight of the mixture, and wherein at least 60% by weight of the linear carboxylic acid component is saturated; and (c) reacting the basic zinc carbonate and the mixture, at an OH:COOH equivalent ratio of from 0.5:1 to 2:1, and at a temperature of from about 130°C. to about 150°C., to form a superbasic zinc soap.

22. A method of stabilizing a halogen-containing plastic material against thermal and/or photochemical degradation, said method comprising:

(a) providing a halogen-containing plastic composition;

(b) providing a superbasic zinc soap prepared by the process according to claims 1; and (c) mixing the halogen-containing plastic composition and the superbasic zinc soap.

\* \* \* \* \*